United States Patent [19]
Linden

[11] Patent Number: 5,915,969
[45] Date of Patent: Jun. 29, 1999

[54] TREATMENT OF TOOTH SURFACES AND SUBSTANCE THEREFOR

[76] Inventor: Lars Åke Linden, Ellahagsvägen 11B, S-187 32 Täby, Sweden

[21] Appl. No.: 09/175,912

[22] Filed: Oct. 20, 1998

[51] Int. Cl.$^6$ .............................. A61C 5/00; A61K 7/20
[52] U.S. Cl. ........................ 433/215; 433/226; 424/53; 424/605; 424/57; 424/49; 523/118
[58] Field of Search ..................... 433/215, 226; 424/53, 605, 57, 49, 613, 52; 523/118; 514/772.6, 152, 773, 777

[56] References Cited

U.S. PATENT DOCUMENTS

| | | | |
|---|---|---|---|
| 5,330,746 | 7/1994 | Friedman et al. | 424/49 |
| 5,403,577 | 4/1995 | Friedman | 424/49 |
| 5,438,076 | 8/1995 | Friedman et al. | 424/49 |
| 5,639,795 | 6/1997 | Friedman et al. | 514/772.6 |
| 5,648,399 | 7/1997 | Friedman et al. | 514/772.6 |
| 5,707,611 | 1/1998 | Ikemura et al. | 424/53 |
| 5,735,942 | 4/1998 | Likowski et al. | 424/49 |
| 5,770,588 | 6/1998 | McNamare et al. | 514/152 |
| 5,820,852 | 10/1998 | Burgess et al. | 424/52 |
| 5,844,019 | 12/1998 | Kato | 523/118 |

*Primary Examiner*—Gene Mancene
*Assistant Examiner*—Pedro Philogene
*Attorney, Agent, or Firm*—Fasth Law Offices; Rolf Fasth

[57] ABSTRACT

A tooth having a tooth surface with a plurality of tubules and microchannels defined therein is treated with a polymeric hydrogel formed by a polyphosphazene substance and a metal salt. The polyphosphazene substance is first applied to the tooth surface and then the metal salt is applied thereto. The polyphosphazene substance is reacted with the metal salt to form a polymeric hydrogel inside the tubules.

14 Claims, 2 Drawing Sheets

FIG. 2
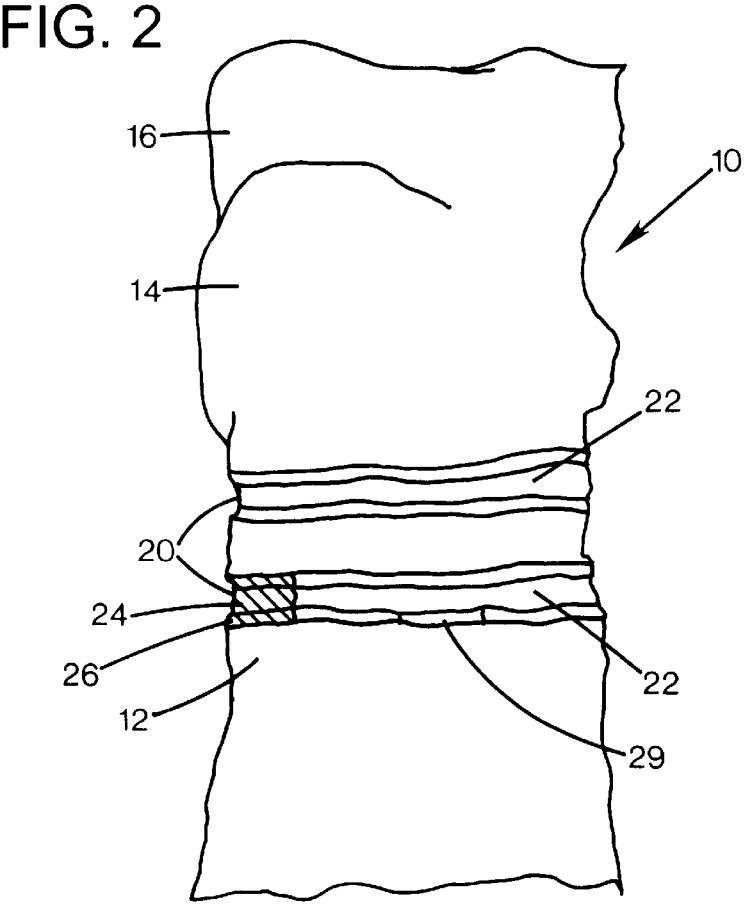
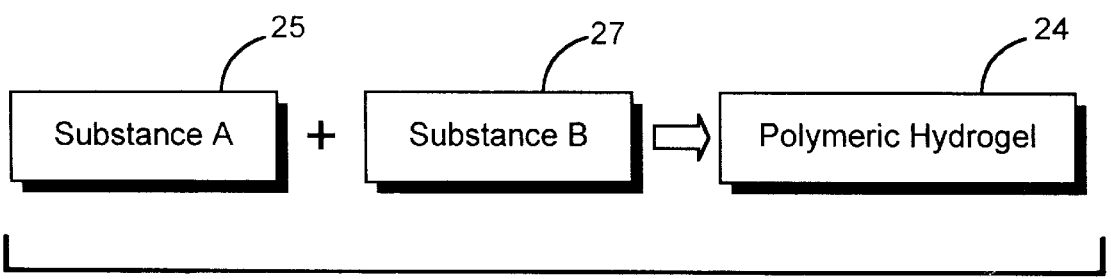
FIG. 3

TREATMENT OF TOOTH SURFACES AND SUBSTANCE THEREFOR

TECHNICAL FIELD

The present invention relates to a method and substance for the treatment of tooth surfaces and sub-surfaces including the treatment of the dentine, enamel and root cement surfaces.

BACKGROUND AND SUMMARY OF THE INVENTION

Almost all human beings suffer from caries for a variety of reasons such as over-consumption of sweet foodstuffs and poor dental care. Many also suffer from hypersensitive tooth necks particularly the middle aged population. It is important for the dental industry to restore, reduce and prevent these problems. However, despite new technologies, the human population is still suffering from caries and sensitive teeth.

It has been found that the hard tissues of human teeth have many very small micro-channels defined therein. The channels penetrate a tooth's major hard components such as the enamel, dentin and root cement and constitute a continuous fluid system that extends from the inside and out to the surface of the tooth. The enamel may be described as an ectodermal tissue composed of rod-shaped structural units that have a diameter of about 4–5 micrometers. The enamel includes large hydroxyapatite crystals embedded in an organic matrix of non-collagenous proteins and lipids. Mesodermal dentin also contains hydroxyapatite crystals but the crystals are smaller and the organic matrix consists of collage and water.

The microchannels are used as a vehicle for providing a means for communication between the interior of the pulp tissue of the tooth and the exterior saliva throughout the life of the tooth. Among other things, the channels often serve as transport ways for ions and molecules through the dental hard tissues to the pulp and out therefrom. The average diameter of these microchannels is about 5–20 manometers in the enamel and about 1–3 micrometers in the dentin, The microchannals are filled with a native biohydrogel of a fibrous protein origin. The native biohydrogel is a natural polymeric material that can swell in aqueous biological fluids and retain a significant amount of fluid.

Whenever the pH falls below 5.5 in the ambient oral environment, some of the hydroxyapatite crystals may dissolve in the microchannels thus widening their lumens. Destructive metabolites and toxins from microorganisms can then easily penetrate the enlarged microchannels. The caries process and bacterial metabolites and toxins may inflame the underlying pulp tissue which may increase the sensitivity of the tooth. The microorganisms may also cause inflammatory reactions in the underlying pulp tissue.

Hypersensitivity of the tooth may arise due to excessive movement of the fluid in the native biohydrogel within the microchannels. The amount of movement of the fluid is partially dependent upon the viscosity of the biohydrogel. However, the native biohydrogel may adversely change its viscosity depending upon such stimuli as the temperature, pH value, ion concentration and electrical potential in the microchannels.

There is a need to make the viscosity of the natural hydrogel more stable and possibly to increase the viscosity thereof to reduce the sometimes painful effect of excessive movement of the fluid that causes hypersensitivity. Any substance used for this purpose should not be allergenic, carcinogenic, mutagenic or toxic. Additionally, the substance should be tasteless, colorless, and not smell and have a viscosity that is suitable for the application on the tooth surface without un-necessarily prolonging the application time. It is also important that the substance does not discolor the dentin over time.

The substance should also be compatible with the native biohydrogel and be able to withstand acid-hydrolytic degradation and biodegradation caused by acids and enzymes present in the oral cavity. The substance should also be able to absorb ions present in the human saliva and to take part in the natural obliteration of the channels with increased age.

Many polymeric hydrogels have been tested in the past. For example, polymeric hydrogels based on polyacrylic acids have a dark color that often tends to darken the color of the dentin. Similarly, salts based on hafnium, titanium and zirconium also have a dark color that may discolor the dentin. Synthetic hydrogels, such as calcium alginate hydrogels, tend to degrade by the microorganisms in the oral cavity. Chitosan hydrogels are often resistant to enzymatic and hydrolytic degradation but the hydrogels are often too fragile and are easily ruptured by mechanical forces. Chitosan hydrogels also suffer from a low water binding capacity and have a low cohesion strength in a gel matrix combination with the native biohydrogel. These drawbacks have reduced the clinical use of chitosan hydrogels.

There is a clinical need to prevent the destructive microorganisms from destroying the microchannels and their native biohydrogels while allowing the natural diffusion of ions and molecules. There is also a need to reduce the fluid flow within the microchannels, to reduce demineralization caused by foreign acids and to increase remineralization by, for example, calcium phosphates and fluoride.

The present invention is a method for treating a tooth having a tooth surface with a plurality of tubules defined therein. The tooth is treated with a polymeric hydrogel formed by a polyphosphazene substance and a metal salt. The polyphosphazene substance is first applied to the tooth surface and then the metal salt is applied thereto. The polyphosphazene substance is reacted with the metal salt to form a polymeric hydrogel inside the tubules.

BRIEF DESCRIPTION OF THE DRAWINGS

FIG. 2 is a detailed view of a portion of a human tooth; and

FIG. 3 is a block diagram showing the reaction between a substance A and substance B to form a polymeric hydrogel.

DETAILED DESCRIPTION

Figure 1:
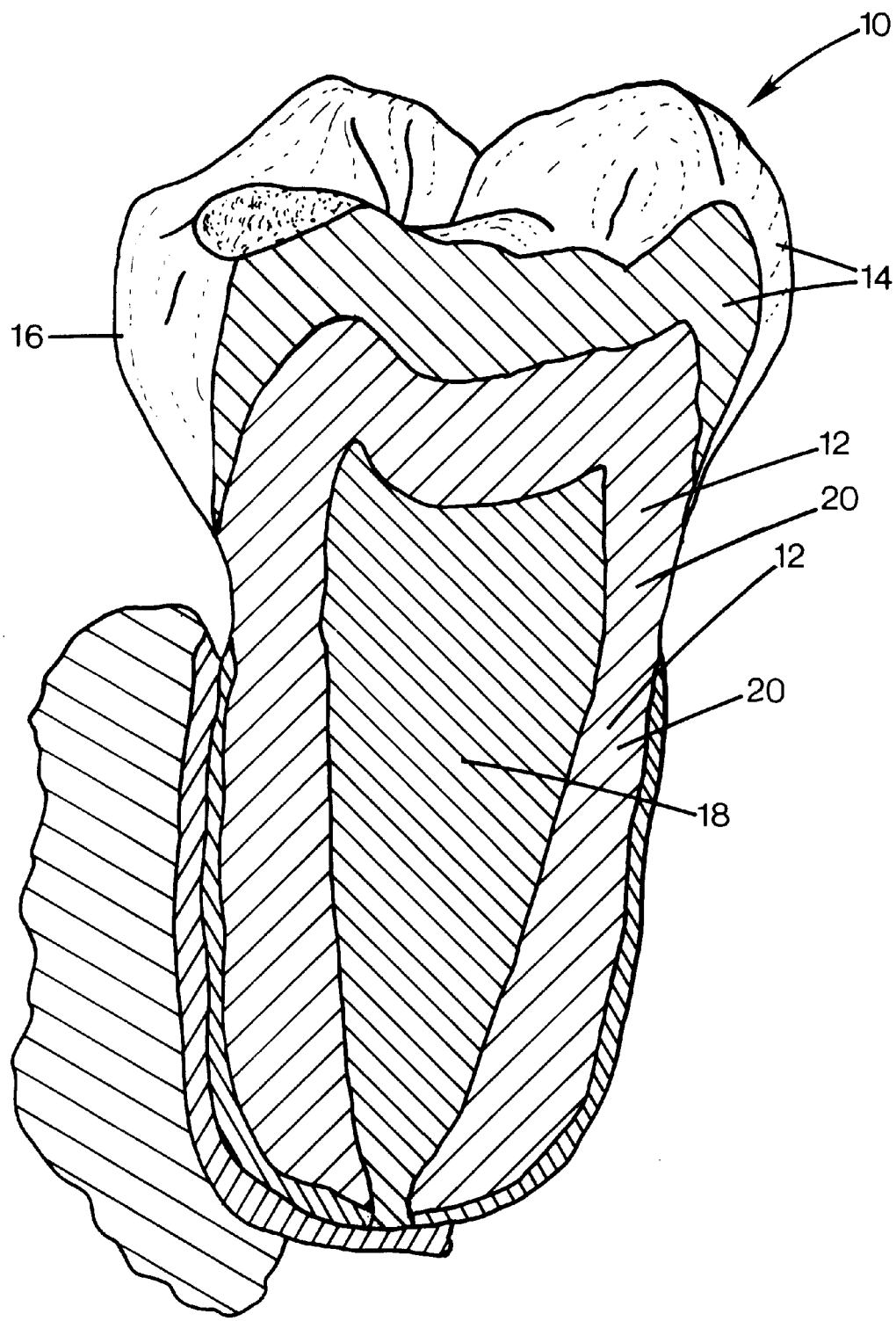
FIG. 1 is a perspective view of a human tooth.

With reference to FIGS. 1–3, a tooth 10 generally comprises a dentine 12 that is covered by an enamel 14 on a crown portion 16 of the tooth 10 and a cement disposed on a root 28 that is part of the tooth. A tooth pulp 18 is disposed inside the dentine 12. The tooth pulp 18 is often a soft, vascular tissue that carries the nerves that may make the tooth sensitive to certain stimuli.

The dentine 12 defines a plurality of microchannels or tubules 20 that have a diameter that is between about 1–3 micrometers. The average diameter is about 1 micrometer at the outer surface and the average diameter increases to about 3 micrometers adjacent the tooth pulp 18. On the outside surface of the dentin 12 of an unworn tooth, such as a tooth on a very young person, the tubules 20 may represent about 1–2% of the total surface area. However, as the dentin is worn or polished, the surface area represented by the tubules 20 is often increased to about 2–4%.

Adjacent the tooth pulp 18, the surface area represented by the tubules 20 is often up to about 10% of the total surface area. One reason for this substantial increase is the fact that there are more tubules 20 adjacent the tooth pulp 18 compared to the outer surface of the tooth and the tubules adjacent the tooth pulp 18 have an average diameter that is greater than the average diameter of the tubules at the outer surface of the tooth.

As best seen in FIG. 2, the tubules 20 contain a native biohydrogel 22 that, among other things, binds water. When caries process starts in the dentine 12, the hydrogel 22 may be dissolved or consumed by micro-organisms and bacteria are allowed to enter the tubules 20 and cause dentine caries. The dissolution of crystals along the inner walls of the tubules 20 may increase the hydraulic permeability of the tubules 20 and and facilitates the penetration of the micro-organisms. Diffusion of bacterial toxins may cause inflammatory reactions in the pulp and give rise to clinical symptoms such as hypersensitivity and pain. The native biohydrogel 22 may form a network and contains about 1–3% positively charged protein substances and the remainder contains water and dissolved ions. The positive charge of the proteins may reduce the ability of the biohydrogel 22 to bind calcium thereto that in turn could obliterate the tubules 20 in an undesirable way. The odontoblast cells disposed in the tooth pulp 18 seem to serve an important function during the formation of the biohydrogel 22. The biohydrogel 22 may also have the function of maintaining the color and elasticity of the vital tooth 10.

The polymeric hydrogel 24 of the present invention is result of a chemical reaction between the phosphazene based polymer 25 (substance A) and a metal salt (substance B) 27. More particularly, the preparation of the polymer 25 or substance A may be divided into several steps including: 1) esterification and preparation of poly(dichlorophosphazene)); 2) reaction of the ester with dichlorophosphazene; 3) hydrolysis; and 4) conversion of the polymer into its salt form.

The esterification step may comprise reacting a parahydroxyphenylcarboxylic acid and ethylhydroxybenzoate to form an ester such as 4'-ethoxycarbonylphenyl 4-hydroxybenzoate or p'-ethoxycarbonylphenyl p-hydroxybenzoate. The esterification may take about one day to perform. During the first hour, the temperature should be held at about 0–5° C. and then be increased to room temperature (about 18–22° C.). Suitable solvents for this reaction include, but are not limited to, methylene chloride and THF. The reaction may be described as shown below:

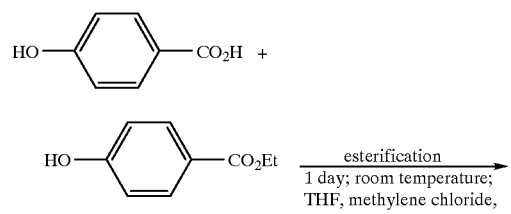

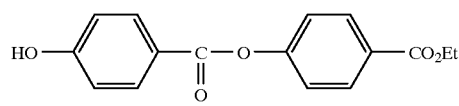

The preparation of poly(diphlorophosphazene) may be performed by thermally polymerizing hexachlorotriphosphazene at about 230–240° C. for about 48 hours to form poly(dichlorophosphazene). The reaction may take place in a sealed tube under vacuum (at a pressure of about 130 Pa) and the polymer may be dissolved in a suitable solvent such as toluene, as shown below:

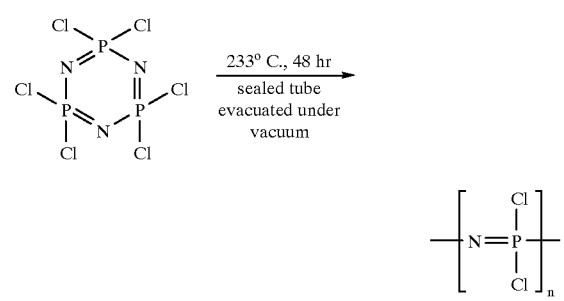

The p'-othoxycarbonylphanyl p-hydroxybenzoate may then be reacted with poly(dichlorophosphazene) for about two days under reflux, as shown below:

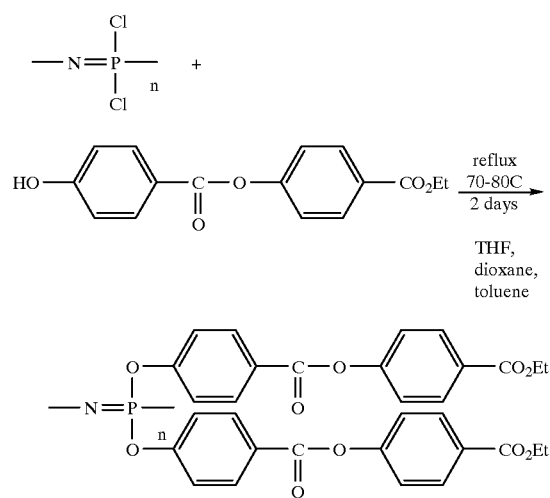

Suitable solvents for the above reaction include, but are not limited to, THF, dioxane and toluene. The ideal temperature depends on the particular mixture but is usually in the range of between about 30° C. and about 50° C. More preferably, the temperature is between about 35° C. and about 40° C. The most suitable temperature range depends on many factors that may affect the reaction.

If the temperature is too low the desired reaction may not start. If the temperature is too high then some undesirable side reactions may take place such as polymer decomposition or degradation and side groups cleavage. A small amount of a catalyst may also be used such as about 3–5% of a tetrabutylammonium bromide. The polymer may also require purification which can take up to a day or two to do. The polymer may be purified by precipitating the polymer from water and then the hexane solution several times, The polymer may be filtered off from the hexane solution. The polymer may then be dissolved in THF before the polymer is again poured into water or the hexane solution. The polymer is then filtered off again and the above steps may be repeated until the desired purity is attained. The polymer may also be continuously extracted with water and then the hexane solution.

The p'-ethoxycarbonylphenyl p-hydroxybenzoate ester may then be hydrolyzed in a THF solution of potassium tert-butoxide $(CH_3)_3CO$-K as the hydrolytic agent to form poly[bis(4-((4-ethoxycarbonylphenyl) oxycarbonyl) phenoxy)phosphazens] or (PCPP-M), which constitutes substance A. Preferably, the reaction mixture is poured into a large amount of water and the dioxane is evaporated. The PCPP-M solution is poured into water to remove inorganic substances that were used during the hydrolysis reaction. It is also possible to let organic solvents evaporate and keep the PCPP-M polymer in the solution in the form of a sodium salt. The PCPP-M is then permitted to precipitate from the solution with hydrochloric acid to convert the PCPP-M polymer into an acidic form that is not soluble in water. It may take an additional day to separate and purify the PCPP-M polymer. The hydrolyzation step may be as shown below:

hydrogel 24 is resistant to dissolution caused by destructive microorganism and may be used to prevent microorganisms from penetrating into the tubules 20 to reduce or prevent the dissolution of the native biohydrogel 22. As best shown in FIG. 2, the hydrogel 24 may serve to mechanically block an entrance 26 into the microchannel 20. The hydrogel 24 is also resistant to acid environments that are caused by bacteria which can ferment carbohydrates (sugars) that are disposed on the tooth surfaces.

If the microchannel 20 is not protected, the acids dissolve the walls of microchannel 20 so that the natural hydrogel fiber come loose from the inner wall. In this way, the acids may penetrate into the microchannels and dissolve the native hydrogels 22. Also, micro-organisms may penetrate into the microchannel and destroy the biohydrogel through phagocytosis and/or enzymatic dissolution. An important feature of the hydrogel 24 of the present invention is that it is resistant to proteolytic enzymes that exist in the saliva.

Another important feature of the hydrogel 24 of the present invention is that it is fully biocompatible with the native biohydrogel 22 when they come into contact with one another. For example, prior art artificial hydrogels often produce HCl when reacted with chlorides, such as $FeCl_3$, which has a negative effect on the native biohydrogel 22. It is important that the formation of hydrogels does not require

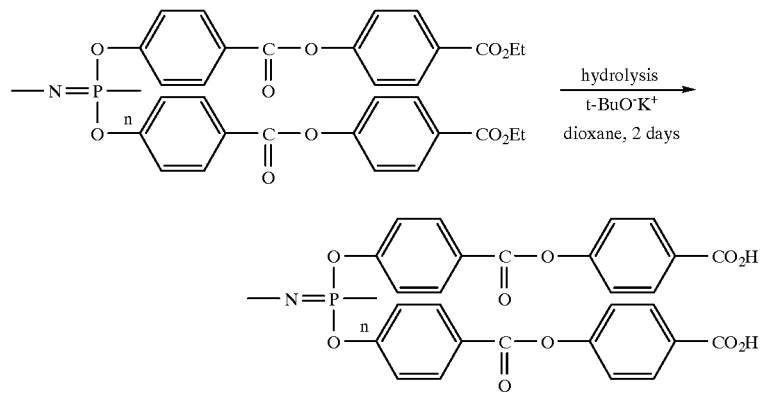

As indicated above, substance B may be a suitable metal salt such as Ca-salt. Suitable calcium salts include calcium chloride, calcium sulphate and other suitable salts. It is to be understood that the substance B may be a salt that is based on any metal that forms ions in water solutions such calcium, titanium, zirconium, hafnium, aluminum and iron. Calcium is preferred because it normally exists in biological systems. Also, the native hydrogel has a positive charge and does not react with the calcium salt so that the calcium chloride may freely diffuse through the native biohydrogel 22.

Iron is not suitable because iron has a tendency to change color during this process which is likely to discolor the teeth in an undesirable way. Also, some of the metal ions may generate a temperature increase during the reaction between the substance B and the substance A that may disturb the delicate balance and flow equilibrium that exist inside the tubules 20. The calcium chloride may be applied onto the dentin surface in the form of a solution that is dripped onto the dentin surface.

If more bridges are created between various PCPP-M polymer chains then a polymer network of the polymeric hydrogels 24 may be formed. The resulting polymeric an extensive expansion that may rupture the delicate network structure of the native hydrogel.

As best seen in FIG. 2, the native biohydrogel 22 is connected to an inner wall of the microchannels 20 with attachment segments 27. The hydrogel 24 may be intermingled with the native biohydrogel 22 without destroying the attachment segments 27. The attachment segments hold the biohydrogel 22 in place and reduce excessive movements of the fluids in the biohydrogel which could be painful.

The hydrogel 24 of the present invention is colorless and does not affect the color of the dentine 12 over time. As indicated earlier, the more the dentin surface is worn or polished the more important it is that the polymeric hydrogel does not discolor the dentin because the surface area as a percentage of the total surface represented by the tubules 20 is increased from about 1–2% at the outer surface to about 10% near the tooth pulp 18.

The hydrogel 24 is preferably applied to the dentin 12 and the enamel 14 every time the native biohydrogel 22 is affected by normal dental procedures such as scraping, laser treatment, drilling and cavity preparation for full and partial crown restorations to protect the native biohydrogel 22 as a preventive measure. The blocking treatment of the dentin 12 with the hydrogel 24 protects the native biohydrogel 22 from both chemicals used in the dental procedure and from bacteria. All treatments of the dentin 12 should include the application of the hydrogel 24 on the surfaces thereof as a preventive measure.

Caries may also affect the enamel 14 and the destructive caries process may penetrate through the enamel 14 into the dentin 12. Even a relatively small entrance into the enamel 14 can create a substantial cavity below the surface of the enamel 14. For example, sugar molecules are only about 3 nanometers in size and may penetrate into the small channels defined in the enamel 14. In this instance, the use of the conventional fluoride treatment may even have a negative effect because the fluoride only binds to and is effective on the outer surface of the enamel 14 while allowing the caries process to continue below the surface of the tooth 10. In general, fluoride only temporarily blocks the outer surface of the microchannels and does not substantially affect the caries processes that may take place below the surface of the enamel 14. In contrast, the hydrogel 24 of the present invention penetrates into the microchannels of enamel and intermingles with the native biohydrogel 22 while blocking the entrances into the channels.

The root cementum may also be treated with the hydrogel 24. The enamel has channels 28 that have an average diameter of between about 3–20 nanometers. Because the polyphosphazene molecule is smaller than about 3 nanometers, the enamel microchannels may also be treated with the hydrogel 24. Similarly, the root cementum has channels with an average diameter between about 0.5 to about 1 micrometer and may be treated also.

In operation, the hydrogel 24 may be applied, for example, to a hypersensitive tooth of a patient. In the preferred method, the first step is to generally clean and brush the tooth surfaces with a cleaning substance such as a chelator (i.e. EDTA in low concentrations), acids and other suitable cleaning substances. For example, the outer surface of the tooth may be cleaned with a 0.1–20% solution of isotonic EDTA (ethylenediamine-tetracetic acid).

The EDTA is preferably isotonic to better penetrate through the remaining smear layer on the tooth 10 due to the fact that hypertonic solutions have a restricting effect on the hydraulic permeability of natural hydrogel due to stearic changes in the hydrogel structure. The isotonic EDTA effectively removes any debris, saliva, smear layer, microorganisms and other substances from the tooth surfaces. Preferably, a 0.5–15% solution of EDTA is used. More preferred, a solution having about 2–6% EDTA is used. Most preferred, a solution having about 3–5% EDTA is used. If the solution has more than 15% EDTA, the solution may have an undesirable taste and the solution may dissolve a portion of the tooth surface due to the low pH of the EDTA at high concentrations. A solution that has less than 0.5% of EDTA may not be powerful enough to effectively clean the tooth surfaces during a relatively short time of application. Other suitable cleaning solutions include phosphoric, citric, polyacrylic and sulphuric acids. The fact that the EDTA is isotonic makes it less likely to affect the flow of fluids in the hydrogel in the tubules 20 because the ion concentration of the isotonic EDTA is very similar to that of the native hydrogeal By increasing the concentration, the penetration possibilities of the hydrogel is reduced. Conventional EDTA has a tendency to increase the flow in the tubules. Undesirable flow in the tubules may negatively affect the diffusion of the polyphosphazene.

A cotton applicator soaked with the polymer 25 or substance A is then applied to the dentin surface. The conversion of substance A may be increased by moving the cotton applicator back and forth on the dentin surface. By increasing the conversion, the diffusion of the substance A may also be increased because the diffusion pressure is increased or at least maintained by constantly adding more substance A to the dentin surface. By maintaining a high concentration of the substance A on the surface a larger amount of the substance A can diffuse into the tubules 20 per time unit. By diffusing the substance A about 100–150 micrometers into the tubules 20, the hydrogel 24 is providing a sufficient protection or blocking function against caries. The native biohydrogel 22 is not a hinder to the diffusion of substance A because the concentration of the biohydrogel 22 is only between about 1–3% and the remainder of the biohydrogel 24 is water. The application time is preferably between about 3 and 5 minutes., However, shorter and longer application time periods may also be used as required. The applicator is then removed and a substance B (such as a calcium salt) is then applied to the dentin surface to chemically react with substance A. The formation of the hydrogel 24 from polyphosphazene and calcium chloride may take place without generating any energy or heat. This means that the native biohydrogel 22 is affected as little as possible.

It may also be necessary to agitate the solution containing the substance B somewhat to improve the diffusion. The substance B, such as calcium chloride, is then permitted to diffuse into the tubules 20 for about 3–5 minutes. The relatively long diffusion process reduces any undesirable disturbances of the native hydrogel and the overall tooth. To protect the area that has been treated, the dentist may cover the area with a temporary protector, such as a vaseline, to permit the diffusion and chemical reaction between the substance A and B to take place in an undisturbed manner. Devices to keep saliva and the tongue away from the area to be treated may also be used. In general, the chemical reaction is not particularly sensitive to saliva. The chemical reaction is more significant and quicker in the beginning and the reaction may continue up to an hour after the application of the substance B.

The PCPP-M polymer is particularly suitable as a substance A due to the polyphosphazene backbone (i.e. alternating nitrogen and phosphorous chain $(-N=P-)_n$) and two side groups of them on each unit). At the ends of the side groups there are carboxylic groups (—COOH) which means that the PCPP-M polymer may be considered as a polycarboxylic acid. However, the carboxylic groups in polyphosphazene are bound to side groups which makes the substance insoluble in water. While the PCPP-M polymer is added to an inorganic salt solution, the PCPP-M polymer is preferably converted into its salt form, e.g. hydrogen (proton, H+) is substituted by inorganic positively charged ions (i.e. —C—O—O—Na+), to make the PCPP-M polymer soluble in water. More specifically, the preparation of the polymeric hydrogel 24 may require dissolving the PCPP-M in a sodium ethoxide, sodium carbonate or sodium ethoxide solution to make the PCPP-M soluble in water. In the preferred method, the PCPP-M polymer is dissolved in sodium ethoxide. A cross-linking agent (substance B) is then added to the solution in order to form a polymer network and hydrogel. Divalent and multivalent positively charged ions such as Ca++, Mg++, Al+++ etc. may be used as the cross-linking agent.

Carboxylic groups have only one negative charge while calcium ions have two positively charged ions which means that one calcium ion can be attached to two carboxylic groups. Therefore, calcium ions may be considered as a bridge between the two carboxylic groups. If one of the carboxylic groups is attached to a PCPP-M polymer chain and the other carboxylic group is attached to another PCPP-M polymer chain then the calcium ion not only form a bridge between two carboxylic groups but also between two PCPP-M polymer chains as shown below:

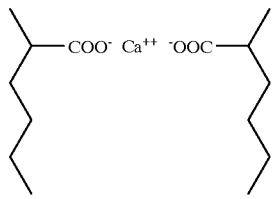

Calcium salts have smaller ions than the substance A and move more easily inside the tubules 20. As soon as the calcium ions penetrate into the tubules 20 they may react with the substance A and form the hydrogel 24, as outlined above. The concentration of organic matters in the tubules 20 may be between about 5–6% after the introduction of the substance A into the tubules 20. The now polymeric hydrogel 24 is, in this way, successively built from the outside and inwardly into the tubules 20 as the calcium ions are penetrating and reacting with the substance A disposed inside the tubules 20. The hydrogel 24 then intermingles with the native biohydrogel 22.

When applying the substance A and B to more than one tooth at a time, it may be necessary to custom build a dispenser that is placed on top of or below all the teeth so that all the teeth are simultaneously first exposed to the substance A and then to the substance B to reduce the total treatment time. The substance A and B may also be applied as mouth-rinse by first applying the solution A for about 3 minutes and then the solution B for another 3 minutes. The substance A and B may also be applied by the patient in the form of a substance A tooth paste that is followed by a substance B tooth paste. One drawback of applying the two substances in a tooth paste form is that the tooth paste itself is a gel that may reduce the penetration effectiveness.

Because only the hydro-dynamics of the biohydrogel 22 are changed when the hydrogel 22 is formed, the sensitivity of the tooth is not dramatically affected during the chemical reaction. The tooth's vitality and physiology are still normal which can be tested by checking the effect of an electrical potential on the tooth by using a pulp tester.

More particularly, when the hydrogel 24 is intermingled with the biohydrogel 22, the hydraulic permeability within the tubules 20 is reduced. This means that the conversion of fluid and dissolved substances into and out of the tubules is also reduced. Because the progression of caries depend upon the conversion rate, it is beneficial to have a relatively low fluid flow within the tubules 20.

Mechanical forces such as chewing tend to increase the conversion rate in the tooth surface and thus increase the progression of the caries process. The reduced fluid flow or conversion by adding the hydrogel 24 in the tubules 20 reduces or even stop the initial caries attack and also the progression of residual caries.

Another benefit of applying the hydrogel 24 of the present invention is that any gaps formed between restorative materials and the body of the tooth may be reduced or eliminated. Conventional fillings, such as amalgams, silicates, glass ionomer cements and composites, do not always fit tightly against the tooth. Over time, gaps may develop due to mechanical forces (such as from chewing) and thermal differences between the food stuffs and the tooth. The widths of the gaps are not stationary but change continuously due to the thermal and mechanical forces. For example, the tooth may be exposed to hot food stuffs followed by cold food stuffs.

The different thermal expansion coefficients between the tooth and the filling material may provide a pumping effect in the gaps and thereby on the hydrogels disposed in the tubules. The pumping effect increases the fluid movement and thus the chemical and physical processes of the caries process. The increase in the conversion of toxic and acidic substances due to the pumping effect may dissolve the hard tooth substance and expose the underlying vital pulp tissue to bacterial toxins.

The combination of the intermingled biohydrogel 22 and the hydrogel 24 of the present invention is flexible and has a swelling pressure that adapt itself to increases and decreases in the width of the gaps and thus may function as a flexible seal during the thermal and mechanical changes of the gaps. The hydrogels 24 may be decomposed by breaking up the bridges by adding monovalent ions such as Na+, K+ so that the concentration of monovalent ions is higher than divalent ions. This brings with it the possibility to renew the protective hydrogel by applying a fresh substance A and followed by a substance B in order to bind new hydrogel to the one earlier applied.

The substance A may be permitted to diffuse into the earlier formed hydrogel 24 and by complexation form a new hydrogel that is interpenetrating the hydrogel 24 and possibly the biohydrogel 22. Due to the good water binding capability and the higher hydrostatic pressure in the new hydrogel together with the non-soluble and bacteriostatic features of the hydrogel 24 there is a permanent protection of gaps between the tooth and the filling. Because the chemical structure of the substance A has —C—O—C—OH— groups in the backbone, it is possible to graft hydroxy groups (OH$^-$)and other active chemical substances to the substance A. The hydroxy-groups may be used to raise the pH value inside the tubules 20 to dramatically reduce or even stop the dissolving of the crystals in the inner walls of the tubules 20. As indicated earlier, the mere presence of the hydrogel 24 also slows down the dissolution process of the crystals although the pH is below 5.5 because the conversion and fluid flow is substantially reduced. By adding a nitrogen chain (—N=) to the backbone of the PCPP-M polymer, many pharmacological substances may be grafted to the PCPP-M polymer. Active substances may be grafted to the substance A.

The presence of hydrogen bonds with a low energy level facilitates the release of their attached companion groups for medical and prophylactic purposes. The hydrogen bond also makes it possible to re-bind new chemical groups so that the hydrogel may be loaded again with active substances. Suitable active substances that can be attached or grafted to the hydrogel include fluoride, chlorhexidine, nitroglycerine, insulin, steroid hormones, peptides, penicillin and cortisone.

The hydrogel 24 may also be used to restore partially dissolved luting materials such as phosphate cement and glass ionomer cement materials. Many luting materials are porous and the hydrogel 24 could be used to penetrate the pores and be mechanically retained in the luting material and function as both a bacteriostatic and chemical barrier.

In alternative method, the hydrogel 24 may be applied to the teeth as a gel. Because the hydrogel 24 forms an interpenetrating network with the native biohydrogel 22 in the tubules 20, a very good retention to the inner walls of the tubules is accomplished. The interpenetrating network between the hydrogel 24 and the biohydrogel 22 is formed at a low speed with only insignificant ruptures of the native hydrogel networks. The PCPP-M polymer is still resistant to hydrolysis and enzymatic degradation.

While the present invention has been described in accordance with preferred compositions and embodiments, it is to be understood that certain substitutions and alterations may be made thereto without departing from the spirit and scope of the following claims.

I claim:

1. A method of treating a tooth having a tooth surface with plurality of tubules defined therein, comprising:

providing a polyphosphazene substance and a metal salt;

applying the polyphosphazone substance to the tooth surface;

applying the metal salt to the tooth surface; and reacting the polyphomphazene substance with the metal salt to form a polymeric hydrogel inside the tubules.

2. The method according to claim 1 wherein the step of applying the metal salt comprises applying calcium chloride to the tooth surface.

3. The method according to claim 1 wherein the step of applying the polyphosphazene substance further comprises permitting the polyphosphazone substance to diffuse into tubules defined in the tooth for between about three minutes and five minutes.

4. The method according to claim 3 wherein the step of applying the metal salt further comprises permitting the metal salt to diffuse into tubules defined in the tooth for between about three minutes and five minutes.

5. The method according to claim 1 wherein the method further comprises grafting a hydroxy group to the polyphosphazene substance and increasing a pH value inside the tooth to a pH value that is above 5.5.

6. A method of treating a tooth having a tooth surface with a plurality of tubules defined therein, comprising:

reacting a carboxylic acid and a benzoate to form an ester;

polymerizing hexachlorotriphosphazene to form dischlorophosphazene;

reacting the ester with the dischlorophosphazene to form a solution;

hydrolyzing the solution to form a phosphazene substance;

purifying the phosphazene substance;

converting the phosphazene substance into an acidic form; and applying the acidic form of the phosphazene substance to the tooth surface.

7. The method according to claim 6 wherein the method further comprises applying a salt to the tooth surface.

8. The method according to claim 7 wherein the tubules comprises a native biohydrogel and the method further comprises reacting the salt with the acidic form of the phosphazene substance to form a hydrogel and intermingling the hydrogel with the native biohydrogel to form an interpenetrating network therebetween.

9. The method according to claim 8 wherein the method further comprises blocking the tubules with the hydrogel.

10. The method according to claim 6 wherein the method further comprises dissolving the phosphazene substance in a solution selected from the group consisting of sodium ethoxide and sodium carbonate.

11. A method of treating a tooth having a tooth surface with a plurality of tubules defined therein, the tubules containing a native biohydrogel, comprising:

providing a polyphosphazene substance and a metal salt;

converting the polyphosphazene substance into a salt form;

cleaning the tooth surface with a cleaning substance;

applying the salt form of the polyphosphazene substance to the tooth surface;

applying the metal salt to the tooth surface;

reacting the polyphosphazene substance with the metal salt to form a polymeric hydrogel inside the tubules; and intermingling the polymeric hydrogel with the native biohydrogel.

12. The method of claim 11 wherein the step of cleaning comprises cleaning with a solution selected from the group of isotonic ethylenediamine-tetracatic, phosphoric, citric, polyacrylic, and sulphuric acids.

13. The method of claim 11 wherein the method further comprises grafting a hydroxy-group to the polyphosphazene substance.

14. The method of claim 11 wherein the method further comprises grafting a grafting substance to the polyphosphazene substance and the grafting substance is selected from the group consisting of fluoride, chlorhexidine, nitroglycerine, insulin, steroid hormones, peptides, penicillin and cortisone.

* * * * *